(12) United States Patent
Ota et al.

(10) Patent No.: US 6,733,492 B2
(45) Date of Patent: May 11, 2004

(54) LASER TREATMENT APPARATUS

(75) Inventors: Yasuo Ota, Gamagori (JP); Hideo Mukai, Toyohashi (JP); Yohei Kamihagi, Nishikasugai-gun (JP); Wataru Niwa, Gamagori (JP)

(73) Assignee: Nidek Co., Ltd., Gamagori (JP)

( * ) Notice: Subject to any disclaimer, the term of this patent is extended or adjusted under 35 U.S.C. 154(b) by 0 days.

(21) Appl. No.: 09/774,592

(22) Filed: Feb. 1, 2001

(65) Prior Publication Data

US 2001/0007068 A1 Jul. 5, 2001

Related U.S. Application Data

(63) Continuation-in-part of application No. 09/577,828, filed on May 25, 2000.

(30) Foreign Application Priority Data

| May 31, 1999 | (JP) | ............................................. | 11-151032 |
| Feb. 10, 2000 | (JP) | ......................................... | 2000-032984 |
| Feb. 10, 2000 | (JP) | ......................................... | 2000-032985 |
| May 8, 2000 | (JP) | ......................................... | 2000-139391 |
| May 8, 2000 | (JP) | ......................................... | 2000-139392 |

(51) Int. Cl.$^7$ .............................................. A61B 18/18
(52) U.S. Cl. .............................................. 606/9; 606/1
(58) Field of Search .............................. 607/88–89, 90; 606/9–17

(56) References Cited

U.S. PATENT DOCUMENTS

| 5,057,104 | A | * | 10/1991 | Chess | ............................. | 606/9 |
| 5,344,418 | A | * | 9/1994 | Ghaffari | ........................ | 606/9 |
| 5,743,902 | A | | 4/1998 | Trost | | |
| 5,820,626 | A | | 10/1998 | Baumgardner | | |
| 5,830,208 | A | * | 11/1998 | Muller | ........................... | 606/9 |
| 6,015,404 | A | * | 1/2000 | Altshuler et al. | .............. | 606/10 |
| 6,059,820 | A | * | 5/2000 | Baronov | ....................... | 606/20 |
| 6,104,959 | A | * | 8/2000 | Spertell | ........................ | 606/31 |
| 6,273,884 | B1 | * | 8/2001 | Altshuler et al. | ............... | 606/2 |
| 6,436,094 | B1 | * | 8/2002 | Reuter | ............................ | 606/9 |
| 6,485,484 | B1 | * | 11/2002 | Connors et al. | ............... | 606/9 |

FOREIGN PATENT DOCUMENTS

| EP | 0 827 716 A2 | 3/1998 |
| JP | 11-514246 | 12/1999 |
| WO | WO 90/12545 | 11/1990 |
| WO | WO 98/07379 | 2/1998 |
| WO | WO 98/24514 | 6/1998 |
| WO | WO 98/51235 | 11/1998 |

* cited by examiner

*Primary Examiner*—Linda C. M. Dvorak
*Assistant Examiner*—Peter Vrettakos
(74) *Attorney, Agent, or Firm*—Oliff & Berridge, PLC

(57) ABSTRACT

A laser treatment apparatus which is used to treat an affected part of a patient by irradiating a treatment laser beam to the affected part is disclosed. The apparatus includes a laser irradiation unit provided with a laser irradiation optical system for delivering the laser beam to the affected part; a contact member including a contact face which is brought into contact with at least one of the affected part and a periphery thereof; a cooler which cools down at least the contact face of the contact member; a sensor which detects at least one of a temperature of a periphery of the contact face made contact with the affected part, a temperature of a predetermined portion of at least one of the contact member and the cooler, a contact state of the contact face with respect to the affected part, and a relative substantially horizontal movement of the contact member with respect to the affected part; and an irradiation controller which controls laser irradiation based on a result of detection by the sensor.

15 Claims, 9 Drawing Sheets

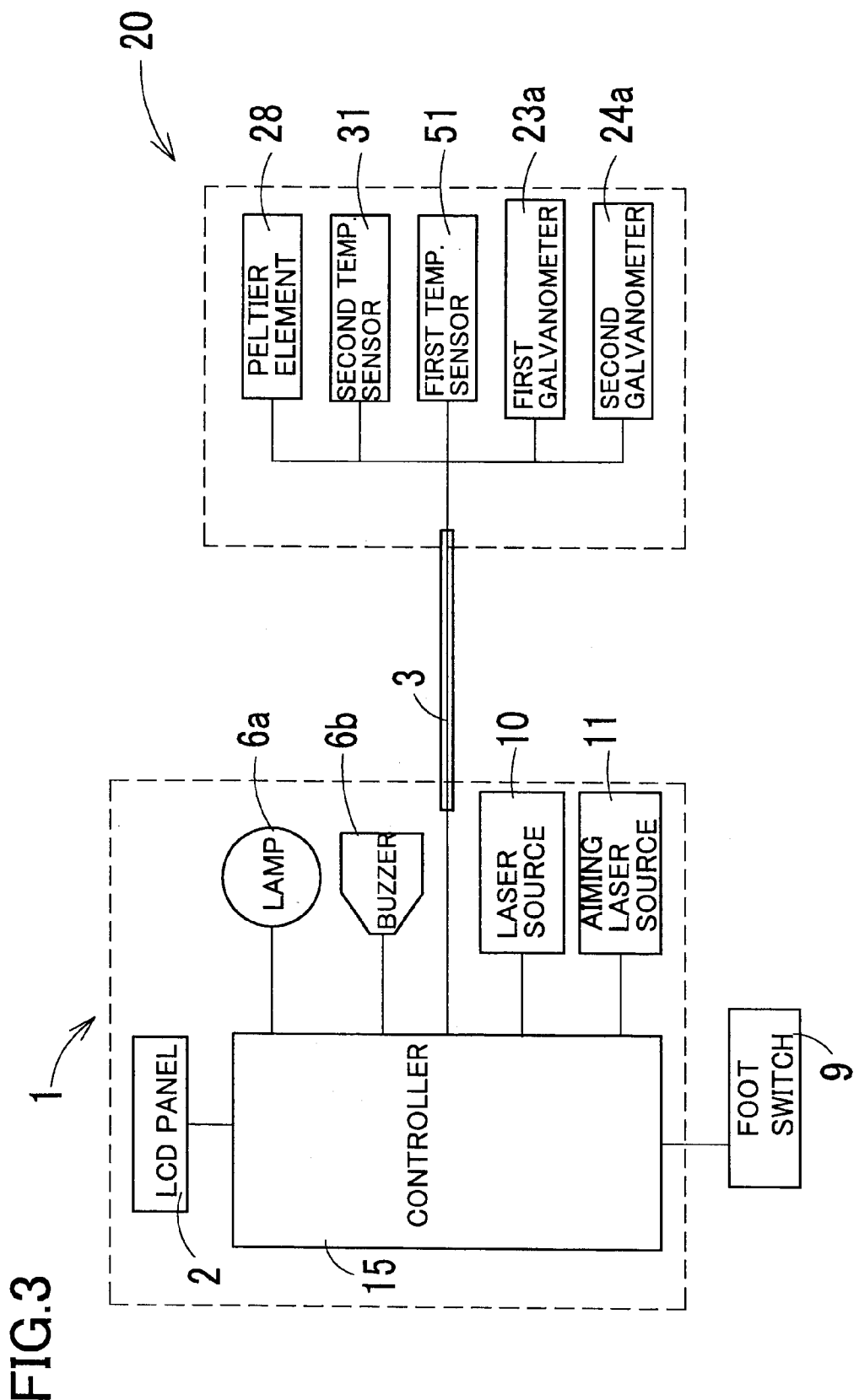

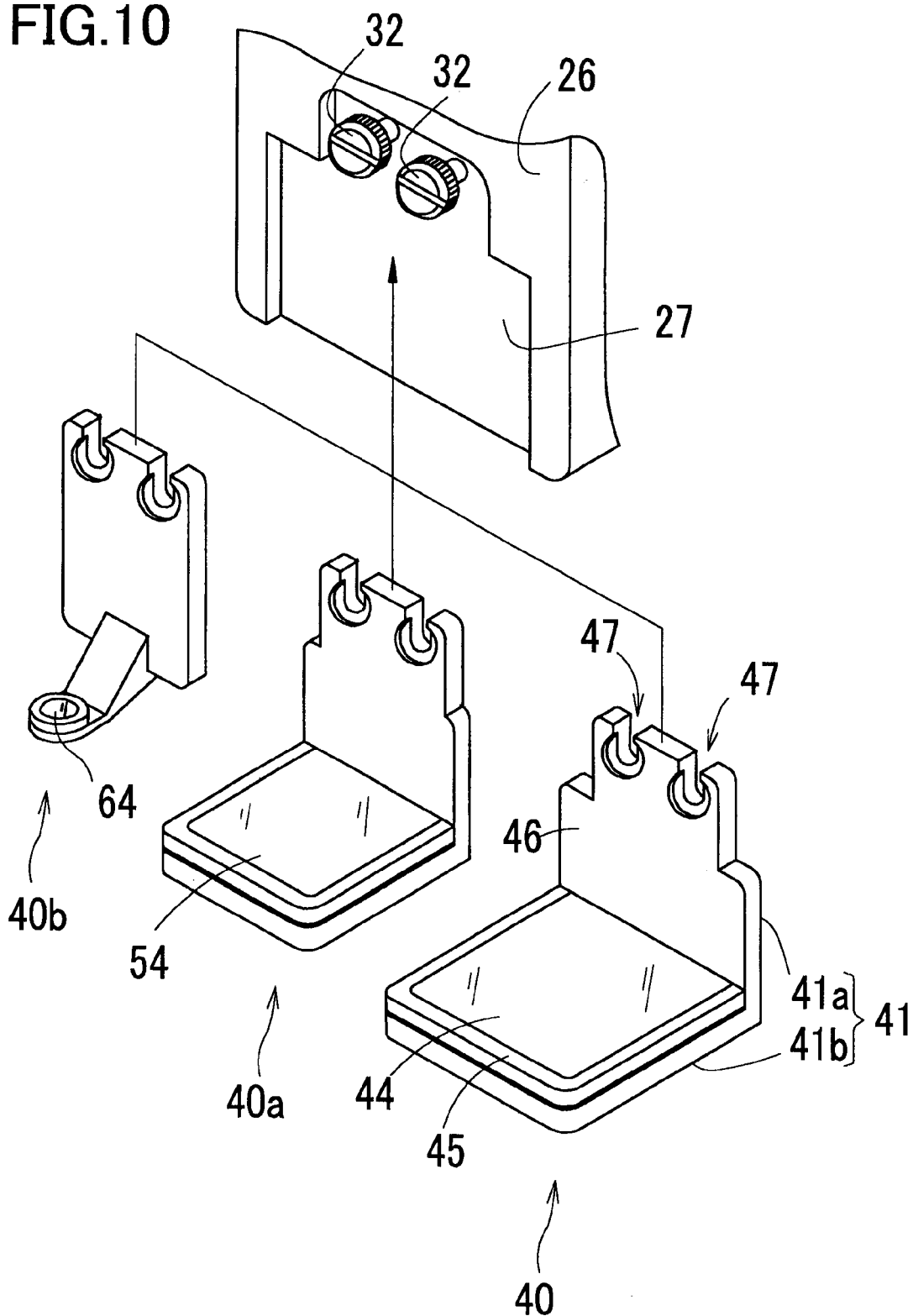

LASER TREATMENT APPARATUS

This is a continuation-in-part application of U.S. patent application Ser. No. 09/577,828 filed May 25, 2000.

BACKGROUND OF THE INVENTION

1. Field of the Invention

The present invention relates to a laser treatment apparatus which is used for treatment such as depilation, removal of wrinkles and birthmarks with a laser beam being irradiated to an affected part (a treatment part) of a patient.

2. Description of Related Art

When a laser treatment apparatus is used for performing treatment such as depilation to a patient by irradiating a laser beam to an affected part of the skin of the patient, the affected part is cooled before the laser irradiation in order to alleviate pain which would be caused by the laser irradiation. As such a method to cool the affected part, conventionally, there have been known a method of spraying nitrogen gas on the affected part and a method of decreasing the temperature of the affected part by making a cooling device contact with the affected part.

For execution of the laser irradiation, the positional relationship between the affected part and a laser irradiation unit such as a handpiece provided in the laser treatment apparatus must be stabilized. Therefore there has been known an apparatus arranged to have a support member (support base) which is brought into contact with the skin for stably supporting the irradiation unit. Furthermore, there is also an apparatus arranged to have a member serving as both the cooling device and the support member.

However, the above conventional apparatus may have possibilities that the laser irradiation is executed when an operator does not intend to do, for example, when the affected part is not sufficiently cooled or when the positional relationship between the affected part and the irradiation unit is not stabilized, etc. In such the cases, the unintentional laser irradiation may cause damage to the affected part and the parts outside thereof. The conventional apparatus is arranged to cool uniformly the affected part in spite of the condition thereof. Thus, the cooling could not be efficiently carried out.

SUMMARY OF THE INVENTION

The present invention has been made in view of the above circumstances and has an object to overcome the above problems and to provide a laser treatment apparatus capable of preventing laser irradiation under inappropriate conditions to an affected part of a patient, and capable of efficiently cooling the affected part.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the purpose of the invention, there is provided a laser treatment apparatus which is used to treat an affected part of a patient by irradiating a treatment laser beam to the affected part, the apparatus including: a laser irradiation unit provided with a laser irradiation optical system for delivering the laser beam to the affected part; a contact member including a contact face which is brought into contact with at least one of the affected part and a periphery thereof; a cooler which cools down at least the contact face of the contact member; a sensor which detects at least one of a temperature of a periphery of the contact face made contact with the affected part, a temperature of a predetermined portion of at least one of the contact member and the cooler, a contact state of the contact face with respect to the affected part, and a relative substantially horizontal movement of the contact member with respect to the affected part; and an irradiation controller which controls laser irradiation based on a result of detection by the sensor.

In the above apparatus according to the present invention, the irradiation controller controls the laser irradiation based on the detection results by the sensor in order to irradiate the laser beam to the affected part only if appropriate conditions for the laser irradiation are satisfied. Accordingly, the laser beam can be prevented from irradiating the affected part under inappropriate conditions for the laser irradiation, thus preventing damage by the laser beam to the affected part of the patient and the parts outside the affected part.

According to another aspect of the present invention, there is provided a laser treatment apparatus which is used to treat an affected part of a patient by irradiating a treatment laser beam to the affected part, the apparatus including: a laser irradiation unit provided with a laser irradiation optical system for delivering the laser beam to the affected part; a contact member including a contact face which is brought into contact with at least one of the affected part and a periphery thereof; a cooler which cools down at least the contact face of the contact member; a first temperature sensor which detects a temperature of a periphery of the contact face made contact with the affected part; and a temperature controller which controls cooling operations of the cooler based on a result of detection by the first temperature sensor.

According to another aspect of the present invention, there is provided a laser treatment apparatus which is used to treat an affected part of a patient by irradiating a treatment laser beam to the affected part, the apparatus including: a laser irradiation unit provided with a laser irradiation optical system for delivering the laser beam to the affected part; a cooler which cools down at least one of the affected part and a periphery thereof; a temperature sensor which detects a temperature of at least one of the affected part and the periphery thereof; and an irradiation controller which controls laser irradiation based on a result of detection by the temperature sensor.

According to another aspect of the present invention, there is provided a laser treatment apparatus which is used to treat an affected part of a patient by irradiating a treatment laser beam to the affected part, the apparatus including: a laser irradiation unit provided with a laser irradiation optical system for delivering the laser beam to the affected part; a contact member which is brought into contact with at least one of the affected part and a periphery thereof; a movement sensor which detects a relative moving amount of the contact member in a substantially horizontal direction with respect to the affected part; and an irradiation controller which controls laser irradiation based on a result of detection by the movement sensor.

According to another aspect of the present invention, furthermore, there is provided a laser treatment apparatus which is used to treat an affected part of a patient by irradiating a treatment laser beam to the affected part, the apparatus including: a laser irradiation unit provided with a laser irradiation optical system for delivering the laser beam to the affected part; a window unit including a first window member having a contact face which is brought into contact with at least one of the affected part and a periphery thereof and a second window member arranged so as to produce a heat-insulating layer between the first and second window members, the first and second window members each having an optical property of transmitting the laser beam; and a cooler which cools down at least the contact face of the first window member.

According to another aspect of the present invention, there is provided a laser treatment apparatus which is used to treat an affected part of a patient by irradiating a treatment laser beam to the affected part, the apparatus including: a laser irradiation unit provided with a laser irradiation optical system for delivering the laser beam to the affected part; a window unit including a window member having a contact face which is brought into contact with at least one of the affected part and a periphery thereof and having an optical property of transmitting the laser beam; and a cooler which cools down at least the contact face of the window member; the laser irradiation unit including a handpiece head provided with a part of the laser irradiation optical system, and the window unit including a plurality of window units having different window members which are of different-sized contact faces, each of the window members being detachable/attachable to the handpiece head.

BRIEF DESCRIPTION OF THE DRAWINGS

The accompanying drawings, which are incorporated in and constitute a part of this specification illustrate an embodiment of the invention and, together with the description, serve to explain the objects, advantages and principles of the invention.

In the drawings,

FIG. 3 is a block diagram of main elements of a control system of the apparatus in the embodiment;

FIG. 10 is an explanatory view showing selectable window units having different shapes and a replacing manner thereof.

DETAILED DESCRIPTION OF THE PREFERRED EMBODIMENTS

A detailed description of a preferred embodiment of a laser treatment apparatus embodying the present invention will now be given referring to the accompanying drawings.

Figure 1:
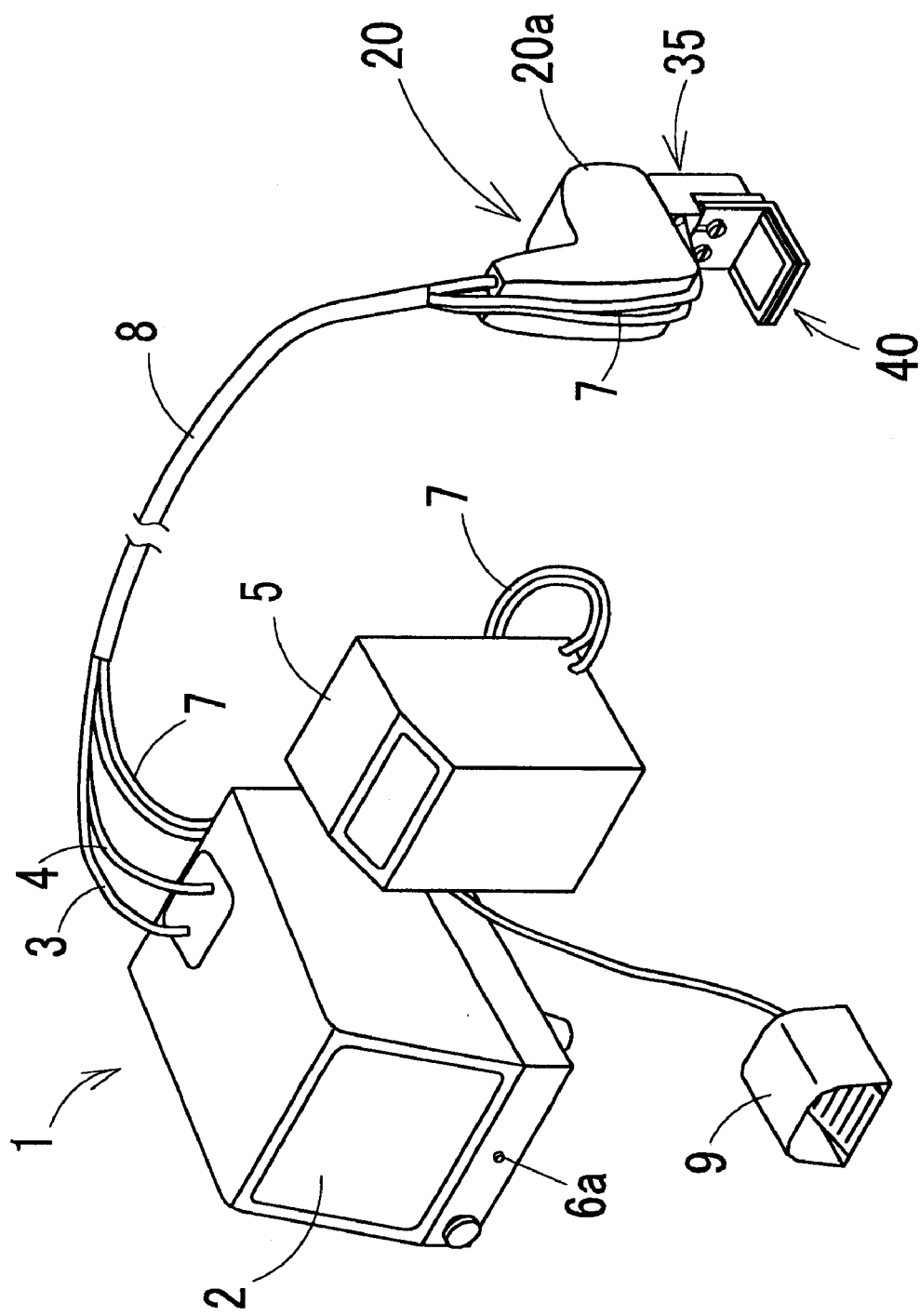
FIG. 1 is a perspective view of a laser treatment apparatus in a first embodiment according to the present invention.

FIG. 1 is a perspective view of a laser treatment apparatus in a first embodiment according to the present invention.

A main unit 1 of the laser treatment apparatus is provided with a large-size liquid crystal display (LCD) 2 at the front face. The LCD 2 is a touch panel whereby an operator can input various settings by depressing operation keys (items) displayed on a screen. A communication cable 3 and a fiber cable 4 are provided extending from the top of the main unit 1 to a handpiece 20 to connect therebetween.

Inside of the main unit 1, there are provided a laser source 10, a laser source 11, and others (see FIG. 3). The laser source 10 emits a near-infrared laser beam of a wavelength of 800–820 nm. This laser beam is used for depilation as a treatment laser beam. The laser source 11 emits a red visible laser beam of a wavelength of 620–650 nm, which is used for aiming. The laser beams emitted from the laser sources 10 and 11 are delivered to the handpiece 20 through the fiber cable 4.

The handpiece 20 is constructed of a scanner head 20a containing an optical system and others for allowing the laser beam delivered thereto through the fiber cable 4 to scan, and a cooling unit (or cooler) 35 for cooling the skin of a patient by contacting with the skin.

Numeral 5 is a chiller for supplying coolant to the handpiece 20 (the cooling unit 35). Two tubes 7 connected with the chiller 5 are made into a bundle together with the communication cable 3 and the fiber cable 4, forming a single convergence cable 8 connected to the handpiece 20. Numeral 9 is a footswitch for generating a trigger signal to instruct start of laser irradiation. Numeral 6a is an indication lamp for informing the operator of that the laser beam is enabled to be irradiated. Numeral 6b is an indication buzzer for informing the operator of the same (see FIG. 3).

Figure 2:
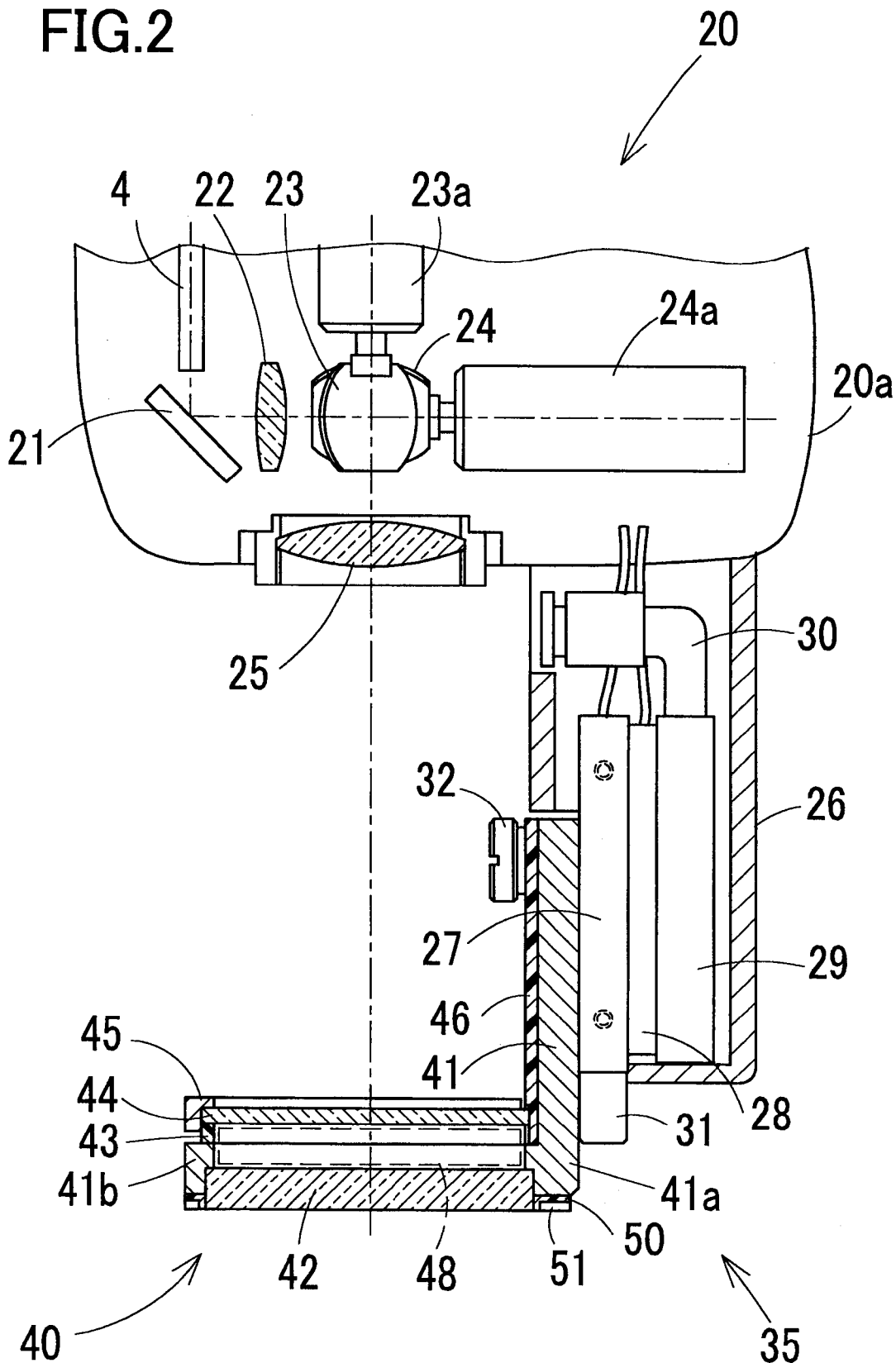
FIG. 2 is a sectional view of a cooling unit and a part of a scanner head of the apparatus in the embodiment.

FIG. 2 is a sectional view of the cooling unit 35 and a part of the scanner head 20a of the handpiece 20. This scanner head 20a includes a first mirror 23 and a second mirror 24. Those first and second mirrors 23 and 24 are rotated (swung) by a first galvanometer 23a and a second galvanometer 24a respectively to deflect a laser beam to move an irradiating point in an X- and Y-directions. The laser beam is thus allowed to scan a wide area.

The laser beam delivered from the main unit 1 through the fiber cable 4 enters the scanner head 20a, wherein the beam is deflected by a mirror 21 and made into parallel luminous flux by a collimator lens 22. Then, the luminous flux is deflected by the first and second mirrors 23 and 24 to move the irradiating point in the X- and Y-directions, passing through a condenser lens 25, thereby forming a circular spot beam, which is of a diameter of about 5 mm in the present embodiment. The laser beam is irradiated as the spot beam onto the affected part (treatment part).

It is to be noted that the position and the focal distance of the condenser lens 25 are determined such that the laser beam projected from the scanner head 20a is focused on or near an underside of a first window 42 (i.e., a contact side with the affected part). Therefore, when the cooling unit 35 (the first window 42) is made contact with the affected part, the scanner head 20a can stably be held at a substantially constant distance from the affected part. The cooling unit 35 also serves as a support member for supporting the scanner head 20a.

The cooling unit 35 is constructed of a scanner support base 26 and a window unit 40. The support base 26 is made of polyacetal resin which has an excellent heat-insulating property. This support base 26 is fixed under the scanner head 20a. A window fixing plate 27 made of aluminum which is good in thermal conductivity is disposed inside the base 26 and is fastened to the base 26 by screws tightened from the side of the base 26 (i.e., perpendicularly to the drawing paper of FIG. 2). Numeral 28 is a Peltier element which is an electronic heat exchanger. This Peltier element 28 is disposed between the fixing plate 27 and a cooling plate 29 made of aluminum and disposed in the base 26. A current is applied to the Peltier element 28 to pass therethrough so that the side contacting with the fixing plate 27 functions as a heat-absorbing side (a cooling side), while the opposite side contacting with the cooling plate 29 functions as a heat-radiating side. The cooling plate 29 is provided therein with a flow passage through which the coolant circulates. The coolant cooled in the chiller 5 is delivered to the cooling unit 35 through the tubes 7 and fed to the cooling plate 29 through a water pipe 30 provided in the cooling unit 35, circulating through the inside of the cooling plate 29. The cooling plate 29 can thus absorb the heat radiated from the Peltier element 28.

Numeral 31 is a second temperature sensor attached to the lower end of the fixing plate 27. This second temp. sensor 31 detects the temperature of the fixing plate 27. The controller 15 controls the temperature of the Peltier element 28 based on the result of detection by the second temp. sensor 31. The detail thereof will be described later.

The window unit 40 is constructed of a window frame 41, the first window 42, a heat-insulating board 43, a second window 44, a cover 45. The details of those members are as follows.

The first window 42 is made of transparent sapphire glass which is good in thermal conductivity. This first window 42 is brought into contact with the skin of the patient for the laser treatment. The window frame 41 has a substantially L-shaped section as shown in FIG. 2, including a vertical part 41a and a horizontal part 41b, and holds the first window 42 in the horizontal part 41b. The heat-insulating board 43 is made of polyacetal resin which has a good heat-insulating property. This board 43 is given the shape of a rectangular frame. The second window 44 is made of transparent glass which is inferior to the first window 42 in thermal conductivity, for example, BK7 (the classification symbol of SHOT Co.) generally used as optical glass. The cover 45 is made of aluminum and has an opening. The window unit 40 having the above arrangement can transmit the laser beam discharged from the scanner head 20a toward the affected part, while supporting the scanner head 20a at a predetermined height on the affected part, or at a predetermined distance therefrom.

The window frame 41 is made of aluminum which is good in thermal conductivity. The vertical part 41a of the frame 41 is formed with two U-shaped slots 47 (see FIG. 10) in the upper portion. Thus, the frame 41 is detachably secured to the fixing plate 27 by two screws 32 passing through the two slots 47 and are threaded into the fixing plate 27. Such the arrangement enables attachment of a suitable window unit according to purposes.

In the present embodiment, besides the window unit 40 mentioned above, for example, a window unit 40a and a window unit 40b may be selectively attached (see FIG. 10). The window unit 40a has a first and second windows 54 with a smaller size (about 30 mm square) than that of the window unit 40. The window unit 40b has a first and second circular windows 64 with a diameter of about 10 mm. This window unit 40b is designed so that each center of the first and second windows 64 is aligned with the optical axis of the condenser lens 25 when the unit 40b is attached to the fixing plate 27. The window unit 40b is therefore mainly used in the case of irradiation of the laser beam without scanning. It is to be noted that the window units 40, 40a, and 40b are different in size and shape, but identical in basic structure.

Detaching the window unit 40 can be easily done by only loosing the screws 32 a little, without fully removing the screws 32, thereby allowing the frame 41 to move downward. On the other hand, attaching the window unit 40 is made by sliding the vertical part 41a of the frame 41 along the fixing plate 27 until the two U-shaped slots 47 of the vertical part 41a are engaged with the two screws 32, and then tightening the screws 32. With the window unit 40 being attached to the fixing plate 27, the fixing plate 27 cooled by the Peltier element 28 cools the window frame 41 contacting therewith, thus cooling the first window 42.

The window frame 41 is formed with an opening in the horizontal part 41b formed horizontally extending and shaped as a rectangular frame. In the underside of the horizontal part 41b, the first window 42 is fitted with adhesive of good thermal conductivity. This first window 42 in the present embodiment is a square of about 40 mm per side. On the upside of the horizontal part 41b, the heat-insulating board 43 is disposed and, furthermore, the second window 44 is fixed on the board 43 with adhesive of a good heat-insulating property to be shielded from the cooling. The cover 45 is adhered to the second window 44 to cover all the above members. With such the arrangement, there is provided a sealed space 48 (indicated by a dotted line in FIG. 2) which serves as a heat-insulating layer between the first and second windows 42 and 44 to enhance the heat-insulation effect between the windows configured as a double-window construction. Accordingly, even if the first window 42 is allowed to cool, the second window 44 will not easily cool. This can prevent the generation of condensation on the upper surface of the second window 44.

It is to be noted that the attachment of the window unit 40 should be performed in dampless environments and therefore it is preferable to reduce the moisture in the air in the enclosed space 48. More preferably, the space 48 is made vacuum. All surfaces of the first window 42 and the second window 44 are desirably each applied with an antireflective film in order to enhance the transmittance of the laser beam.

Numeral 50 is a heat-insulating board 50 made of polyacetal resin which has a good heat-insulating property. This board 50 is disposed, as shown in FIG. 2, between the window frame 41 and a first temperature sensor 51 and between the first window 42 and the first temp. sensor 51 to prevent the first temp. sensor 51 from making contact with both of the window frame 41 and the first window 42.

Figure 4A:
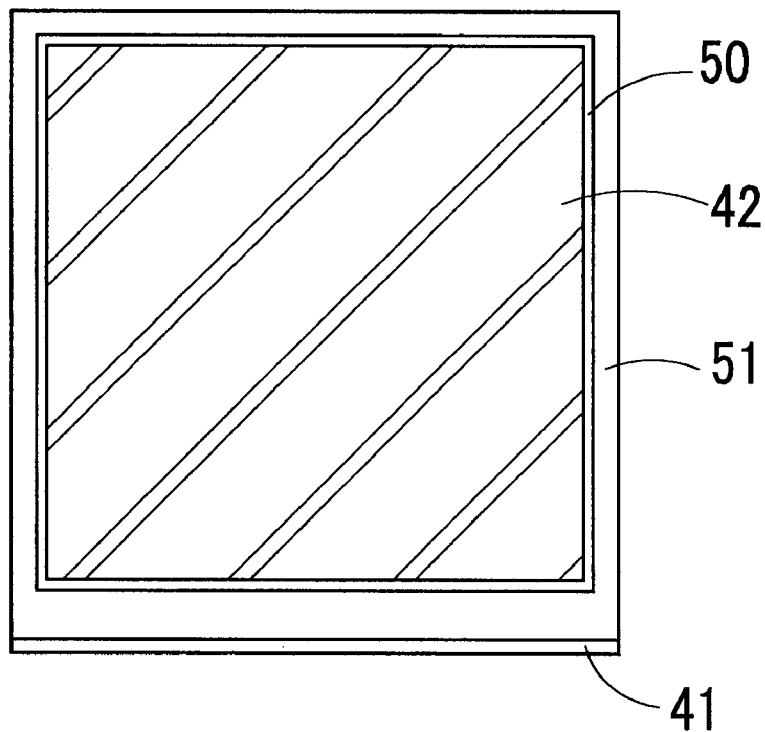
FIG. 4A is a bottom view of a window unit of the apparatus.

The first temp. sensor 51 is constructed of a sheet-type thermistor. This sensor 51 is attached to the window frame 41 along the frame shape of the bottom surface of the horizontal frame part 41b (see FIG. 4A) so that the surface of the first temp. sensor 51, opposite to the surface contacting with the heat insulating plate 50, becomes substantially flush with the bottom surface of the first window 42. Thus, when the bottom surface of the first window 42 is brought into contact with the skin of the patient, the surface of the first temp. sensor 51 makes contact with the skin at the same time, enabling detection of the temperature of the skin (the periphery of the affected part).

Figure 4B:
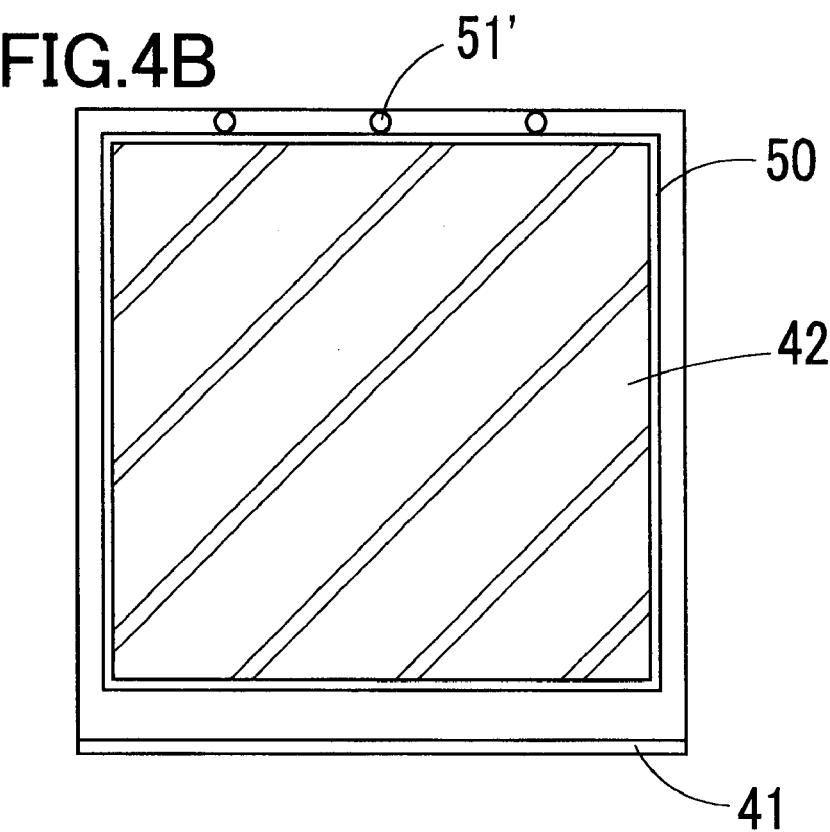
FIG. 4B is a bottom view of a window unit in another example.

It is to be noted that although the first temp. sensor 51 is a sheet-type thermistor in the present embodiment, it is not limited thereto and may be modified to different arrangements if only the surface thereof can make contact with the skin to detect the temperature thereof at the same time when the bottom surface of the first window 42 is brought into contact with the skin. One example of such the arrangements is shown in FIG. 4B. In FIG. 4B, a first temp. sensor 51' is constructed to detect the temperature of a point on the skin.

The first temp. sensor 51 is connected to the communication cable 3 through a connection cable not shown and a connector. At the time of detaching the window unit 40, the connection cable is disconnected from the connector. This also enables an exchange of window units without any trouble.

Similarly to the case of the second temp. sensor 31 mentioned above, the controller 15 controls the temperature of the Peltier element 28 based on the detection result by the first temp. sensor 51. The detail thereof will be described later.

Numeral 46 is a heat-insulating board made of polyacetal resin and is fixedly attached to the vertical part 41a of the window frame 41 for preventing the window frame 41 from absorbing extraneous heat and also for heat-insulating the second window 44.

Next, operation of the laser treatment apparatus constructed as above will be described with reference to FIG. 3 which is a block diagram of main elements of a control system of the apparatus in the present embodiment.

The first galvanometer 23a, the second galvanometer 24a, the second temp. sensor 31, the first temp. sensor 51, the Peltier element 28, and others are connected to the controller 15 through the communication cable 3.

An operator selects a window unit having an appropriate size corresponding to the position and size of an area to be irradiated with the laser beam and attaches the selected one to the fixing plate 27. For example, if the affected part is flat and large, the window unit 40 is used to allow the laser irradiation (scan) on a wide area. If the affected part is small, on the other hand, the window unit 40a is used to minimize the contact area of window with the skin of the patient outside the affected part, preventing the skin outside the laser irradiation area from being cooled, thus reducing a burden on the patient. If the affected part is in an area of an irregular shape such as the face, armpit, or abdomen of the patient, the use of the window unit 40a or the window unit 40b is suitable. This is because those unit 40a and 40b have a good operability with respect to a small affected part. In particular, the window unit 40b is conveniently used with respect to a smaller affected part or a largely uneven area such as the vicinity of the nose, mouth, or eye.

The operator operates setting keys displayed on the LCD panel 2 to set irradiation conditions for preparation for laser irradiation. A single mode is set in the case where the window 40b is attached. Alternatively, a scan mode is established in the case where the window unit 40 or 40a is attached. The shape of a scanning pattern may be selected from the patterns stored in advance in a memory of the controller 15. In the present embodiment, as the patterns, there are prepared a circular pattern, a square pattern, a rectangular pattern, a linear pattern, etc. The following description is made on the case where the window unit 40 has been attached.

While the first window 42 is not in contact with, or is apart from the affected part of the patient, the controller 15 controls the temperature of the Peltier element 28 so that a predetermined value is constantly detected by the second temp. sensor 31.

The contact/noncontact of the first window 42 with the affected part can be judged based on the result of temperature detection by the first temp. sensor 51. For instance, the threshold value for detection of the contact of the first window 42 with the affected part is set at 30° C. When the first temp. sensor 51 detects the temperature more than 30° C., the controller 15 judges that the first window 42 is in contact with the affected part. Alternatively, a contact sensor (a touch sensor) may be provided in the part or surface of the window unit 40 which is made contact with the skin.

While the controller 15 controls the temperature of the Peltier element 28 based on the result of temperature detection by the second temp. sensor 31, the controller 15 controls (interlocks) the laser source 10 to prevent the laser irradiation even if a trigger signal of instructing the laser irradiation is input from the footswitch 9. Alternatively, instead of direct driving of the laser source 10, a safety shutter may be controlled to be inserted into or removed from an optical path of the laser beam.

The operator, after preparation of the main unit 1 for laser irradiation, holds the handpiece 20 by hand to bring the first window 42 into contact with the affected part (skin). Then, the controller 15 receives the result of detection by the first temp. sensor 51 and determines whether the detected temperature is equal to or more than the threshold value to detect the contact of the first window 42 with the affected part. When the detected temperature is the threshold value or more, the controller 15 recognizes that the first window 42 is in contact with the affected part. Upon recognition of the contact of the first window 42 with the affected part, the controller 15 stops control of the temperature of the Peltier element 28 based on the detection result by the second temp. sensor 31 and, alternatively, starts the control of the temperature of the Peltier element 28 based on the detection result by the first temp. sensor 51.

Contacting with the first window 42, the affected part is gradually cooled due to heat-absorption by the first window 42. The temperature variation occurring in the affected part also causes the temperature of the periphery of the affected part to decrease. The first temp. sensor 51 detects the temperature variation in the affected part and the periphery thereof.

When the temperature of the affected part detected by the first temp. sensor 51 does not reach an appropriate value (for example, 5° C. in the present embodiment, which is referred to as a predetermined temperature) for laser irradiation, the controller 15 controls the temperature of the Peltier element 28 (the heat-absorbing side, or the cooling side) to further decrease regardless of the temperature detected by the second temp. sensor 31.

Decreasing the temperature of the heat-absorbing side of the Peltier element 28 enhances the heat-absorbing effect of the first window 42. This makes it possible to shorten the time needed until the temperature of the affected part reaches (decreases to) the predetermined temperature. When the detected temperature by the first temp. sensor 51 reaches the predetermined temperature, the controller 15 stops cooling the Peltier element 28. Simultaneously, the controller 15 releases the interlock of the laser source 10 to enable the laser beam to be irradiated to the affected part. Alternatively, the safety shutter may be removed from the optical path for enabling laser irradiation. The controller 15 causes the indication lamp 6a to light up and the indication buzzer 6b to sound in order to inform the operator of that the temperature of the affected part has reached the predetermined temperature and the laser irradiation is enabled.

After the indication by the lamp 6a and the buzzer 6b, the operator may instruct the laser irradiation by depressing the footswitch 9. Upon receipt of the trigger signal from the footswitch 9, the controller 15 controls the first and second galvanometers 23a and 24a respectively to allow the laser beam emitted from the laser source 10 to scan a selected scanning area in the treatment part while irradiating. Alternatively, the controller 15 may be arranged to automatically start the laser irradiation upon release of the interlock of the laser source 10.

Upon completion of the laser irradiation, the first window 42 (the handpiece 20) is moved away from the affected part. This causes sudden variation in temperature detected by the first temp. sensor 51 because the sensor 51 detects the room temperature. When the controller 15 obtains a predetermined or more temperature variation (for example, a 5° C. or more variation) in the detection result by the sensor 51 after completion of the laser irradiation, the controller 15 recognizes that the first window 42 has been moved away from the affected part, and controls the temperature of the Peltier element 28 based on the detected temperature by the second temp. sensor 31.

In the above first embodiment, the temp. sensor (the first temp. sensor 51) is provided near the first window 42 to directly detect a variation in temperature of the affected part. With this detection manner, the laser irradiation is controlled so that it is precluded until the detected temperature reaches the predetermined value. However, the laser irradiation may also be controlled by the arrangements other than that described above. Some examples thereof will be described below.

In a second embodiment, the laser irradiation is controlled by indirect detection of the temperature of the affected part, instead of the direct detection of the same in the first embodiment. This indirect detection is executed by detecting a variation in temperature of the first window 42.

Figure 5:
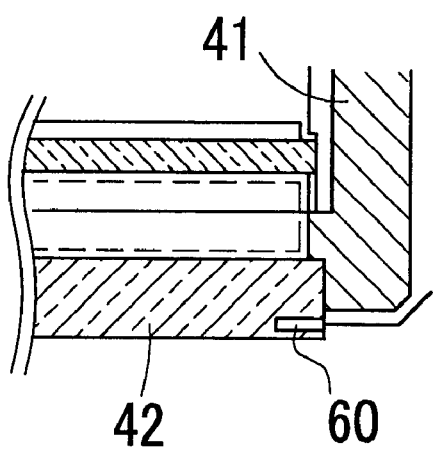
FIG. 5 is a sectional view of showing a structure of indirectly detecting temperatures of an affected part in a second embodiment of the apparatus.

In the present embodiment, a temperature sensor 60 for detecting the internal temperature of the first window 42 is provided in the first window 42 at a position where the sensor 60 does not prevent the scanning of the laser beam (see FIG. 5). When the first window 42 held at a predetermined temperature is made contact with the skin, the temperature of the window 42 rises once. The window 42 is then cooled by the Peltier element 28 into the predetermined temperature again. The controller 15 enables the laser irradiation when the temperature of the window 42 returns to the predetermined value (or reaches a permissible range of the predetermined temperature). In this case, the temp. sensor 60 is preferably disposed inside the first window 42 closer to the bottom surface (as closer as possible to the affected part), thus enabling speedup in detection of temperature variation.

Figure 8:
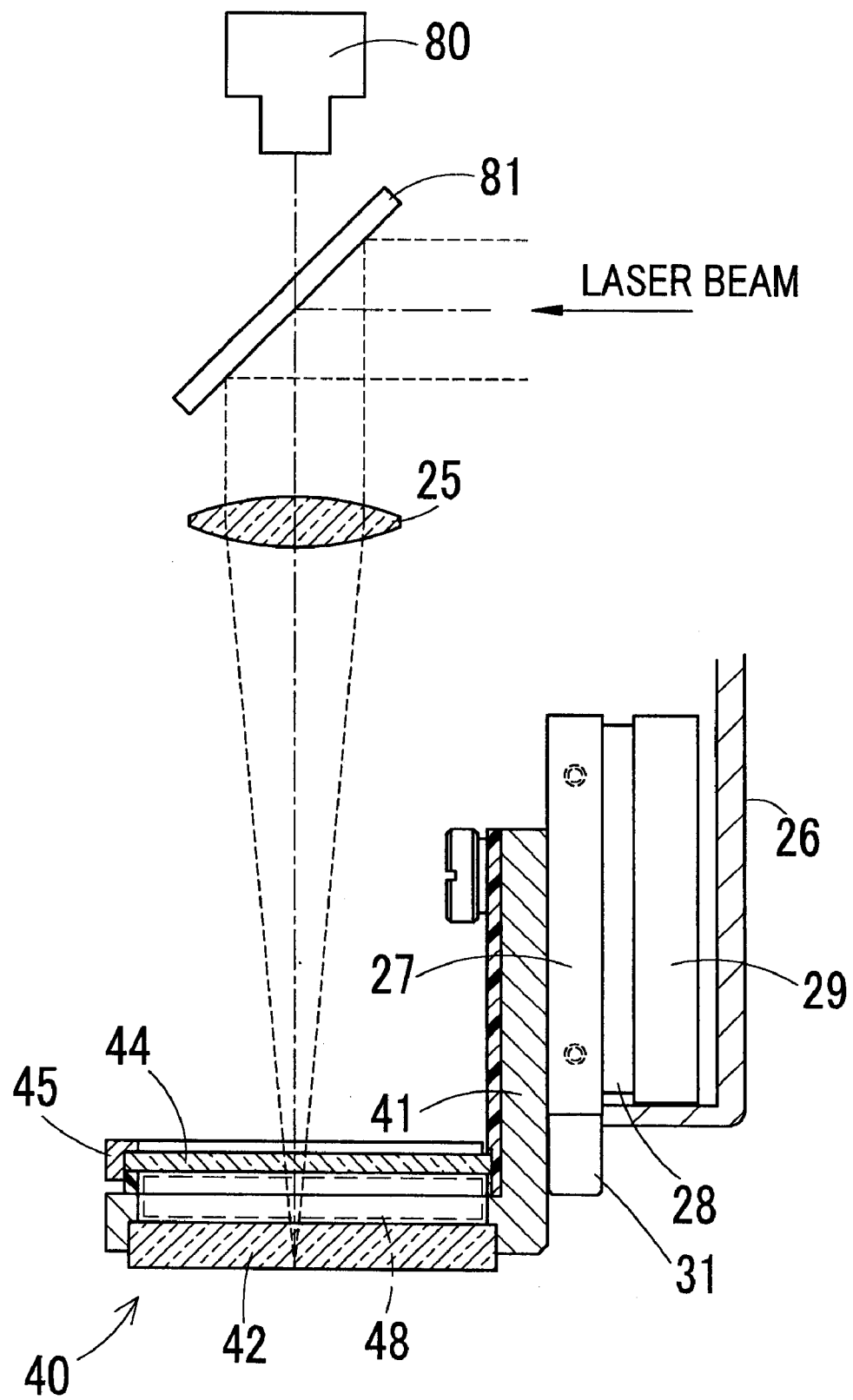
FIG. 8 is a schematic view of a structure of detecting temperatures of an affected part by use of a temperature sensor of a non-contact type in a third embodiment of the apparatus.

In a third embodiment, a noncontact type temperature sensor is used to detect the temperature of the affected part through the first window 42 and others. This arrangement is shown in FIG. 8, where like elements corresponding to those in FIG. 2 are indicated by like numerals. Numeral 80 is a temperature sensor disposed in the scanner head 20a. The sensor 80 detects infrared energy radiated from the affected part to detect the temperature of the affected part. Numeral 81 is a half mirror which reflects the major part of the laser beam, while transmitting an infrared light from the affected part.

Figure 9:
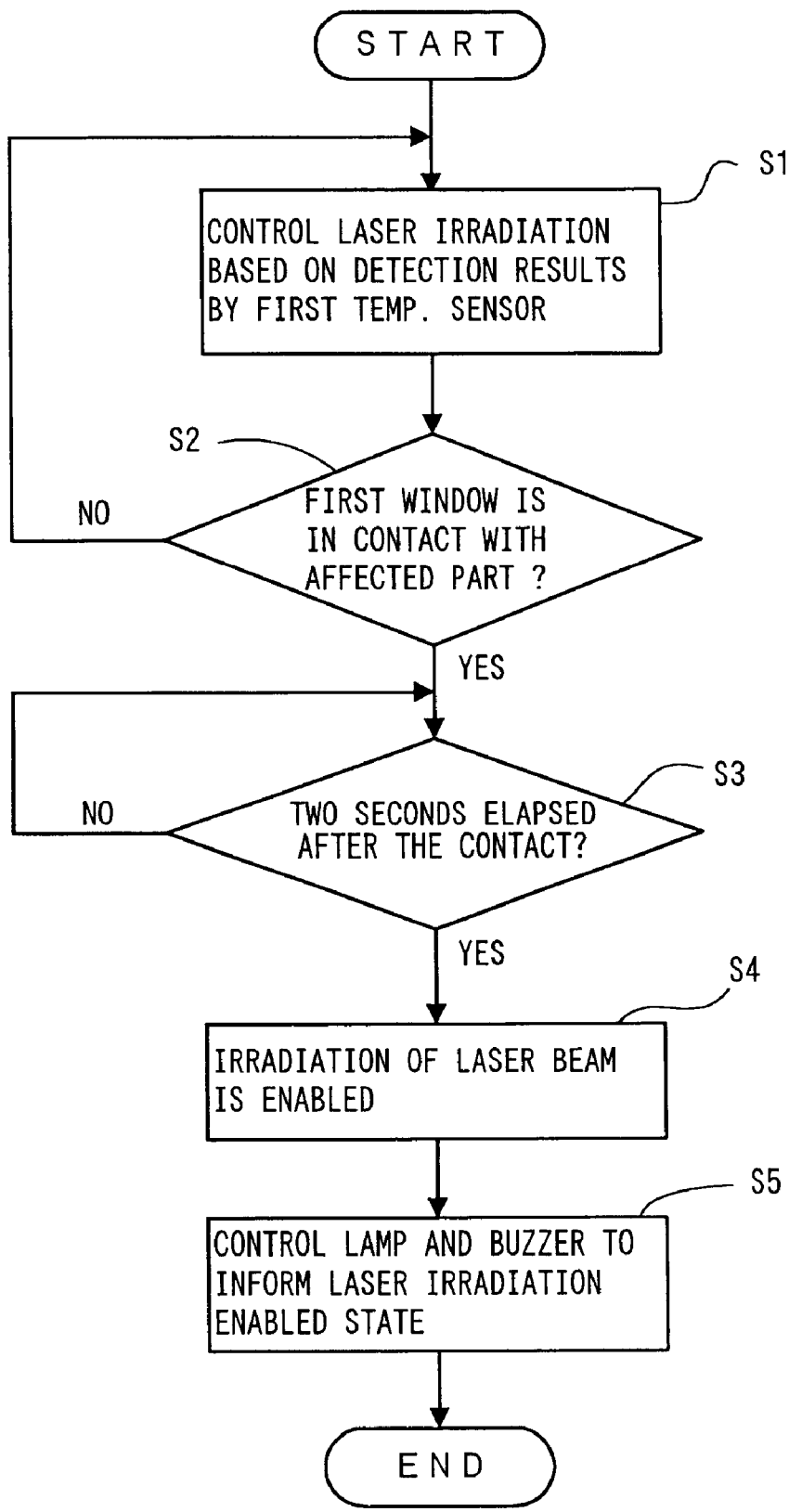
FIG. 9 is a flowchart of showing laser irradiation control in a fourth embodiment of the apparatus.

In the above embodiments, the laser irradiation is controlled based on the temperature of the affected part, but it is not limited thereto. It may be arranged, for example, such that the laser irradiation is enabled when a predetermined time elapses after detection that the first window 42 is in contact with the affected part. The control in this case is explained below as a fourth embodiment, referring to FIG. 9 showing a flowchart of the laser irradiation control.

After preparation of the main unit 1 (S1), the operator holds the handpiece 20 to bring the first window 42 into contact with the affected part. The controller 15 then determines whether the detected temperature by the first temp. sensor 51 (or the temp. sensor 60 or 80) is the threshold value or more (S2). When the detected temperature is the threshold value or more, the controller 15 recognizes that the first window 42 is in contact with the affected part (S2: YES). The controller 15 enables the laser irradiation after a lapse of a predetermined time (for example, 2 seconds in the present embodiment).

This predetermined time can be determined in the following manner. The first window 42 is in advance made contact with some different positions in the affected part to obtain a time needed until the temperature at each position reaches a proper value. Thus the controller 15 quantitatively determines the predetermined time. It may be arranged such that the controller 15 simultaneously detects a temperature variation occurring in the affected part through the first temp. sensor 51 (or the temp. sensor 60 or 80) and, when the temperature reaches the predetermined value before a lapse of the predetermined time, the laser irradiation is enabled even if the predetermined time does not lapse yet.

Furthermore, in a fifth embodiment, the laser irradiation may be controlled by only detection of contact/noncontact of the first window 42 with the affected part. In this case, the controller 15 detects the contact state of the window 42 based on a temperature variation detected by the first temp. sensor 51 (or the temp. sensor 60 or 80). The laser irradiation can thus be controlled based on the detection result by the sensor 51. Alternatively, two electrodes may be provided in a face of the window unit 40 which makes contact with the affected part, allowing the controller 15 to detect variation in current or resistance which occurs when the electrodes come into contact with the affected part. Instead thereof, a pressure detecting element may be used to allow the controller 15 to determine the contact/noncontact state of the first window 42, for example, by detecting a pressure exerted on the first window 42 when made contact with the affected part.

Figure 6:
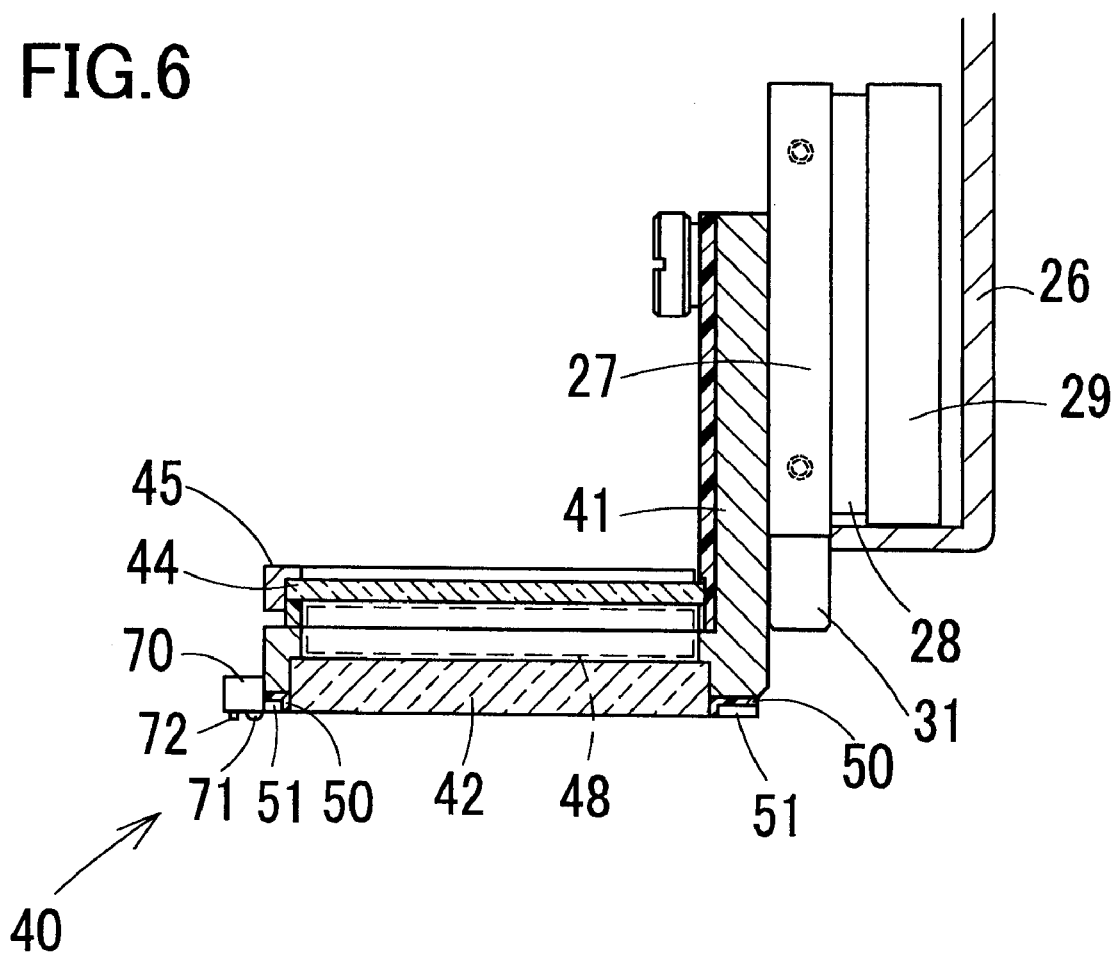
FIG. 6 is sectional view of showing a structure of detecting relative movements of a handpiece to the an affected part in a sixth embodiment of the apparatus.

In a sixth embodiment, on the other hand, the laser irradiation control can be executed if the handpiece 20 and the patient unintentionally move even during the laser irradiation. This arrangement is explained below with reference to FIG. 6. FIG. 6 shows the structure of the handpiece 20 shown in FIG. 2 with a contact section 70 added. Like elements corresponding to those in FIG. 2 are indicated by like numerals. The contact section 70 is provided with detecting members for detecting the contact state of the first window 42 with the affected part and the movement thereof in a substantially horizontal direction.

To be more specific, at the underside of the contact section 70 are provided a ball 71 and a microswitch 72. The ball 71 is rotatably held in the contact section 70 so as to partially protrude out of a housing of the contact section 70. The microswitch 72 is turned on when the underside of the contact section 70 comes into contact with the affected part.

Figure 7A:
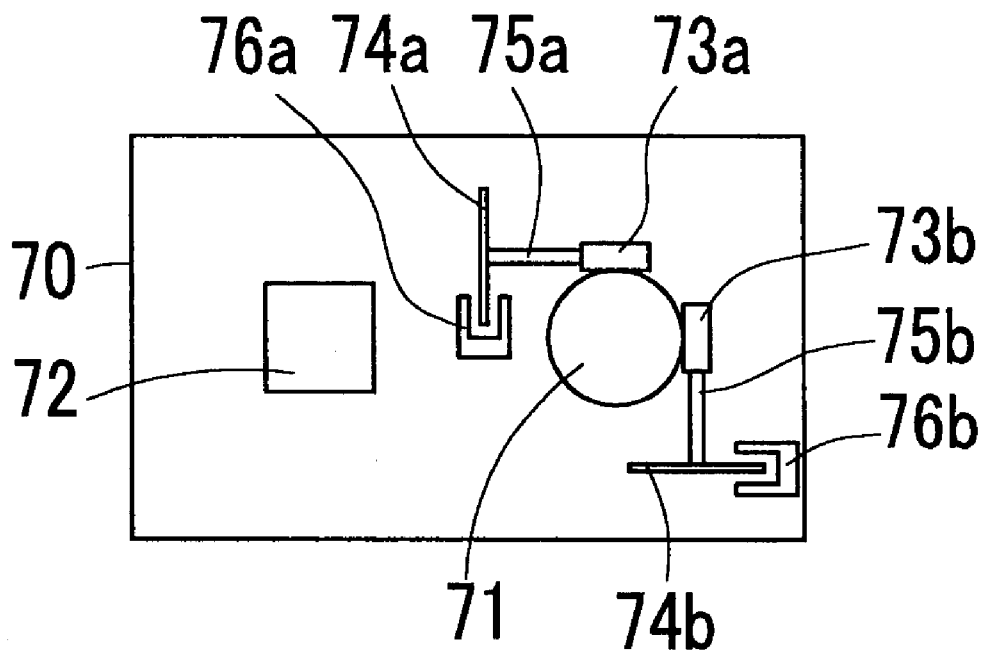
FIG. 7A is a schematic view of an internal structure of a contact section, seen from bottom, in the sixth embodiment.

FIG. 7A is a schematic view of the internal structure of the contact section 70, seen from bottom. Rollers 73a and 73b are rotatably provided in contact with the ball 71, both rollers being disposed in directions intersecting at right angles. Rolling of the ball 71 causes the rollers 73a and 73b to rotate respectively. Numerals 74a and 74b are rotating discs which are attached to shafts 75a and 75b of the rollers 73a and 73b, respectively. By rotation of the rollers 73a and 73b, the rotating discs 74a and 74b are rotated in the same directions as those of the rollers 73a and 73b.

Figure 7B:
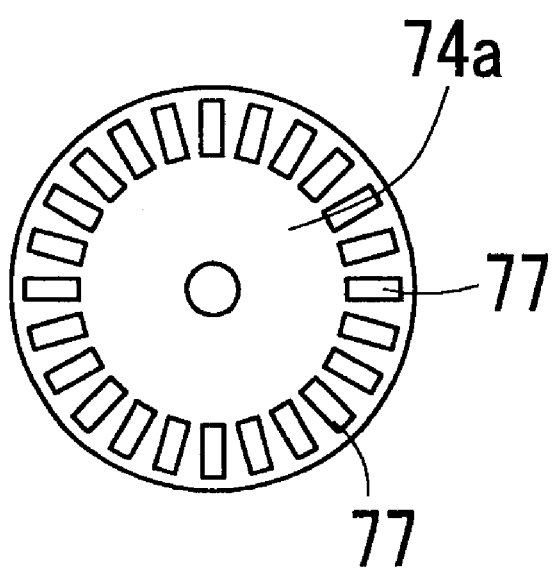
FIG. 7B is a front view of a rotating plate of the contact section in the sixth embodiment.

Each of the rotating discs 74a and 74b is provided with a plurality of slits 77 circumferentially spaced as shown in FIG. 7B. Numerals 76a and 76b are photosensors, each of which is constructed of a light projecting element and a light receiving element. The photosensor 76a (76b) is disposed so that the rotating disc 74a (74b) is partially inserted between the light projecting element and the light receiving element. This mechanism is substantially similar to a movement detecting mechanism of a mouse generally used in personal computers.

The microswitch 72 and the photosensors 76a and 76b are connected to the controller 15 through the communication cable 3.

After preparation of the main unit 1 for the laser irradiation in a similar manner to the above embodiments, the operator moves the handpiece 20 by hand to bring the first window 42 into contact with the affected part. When the first window 42 is made contact with the affected part, pressing the microswitch 72, thereby transmitting a relevant signal to the controller 15 through the communication cable 3.

If the controller 15 has not received the signal from the microswitch 72, alternatively, if the temperature of the affected part has not reached the predetermined value, the controller 15 controls (interlocks) the laser source 10 to preclude the irradiation of the laser beam even if the trigger signal of instructing the laser irradiation is input.

Even though the laser irradiation is enabled and executed, the handpiece 20 or the patient unintentionally moves or shifts in some cases, thereby causing the contact section 70 to separate from the affected part. The microswitch 72 is thus turned off. Receiving no signal from the microswitch 72, the controller 15 stops the laser irradiation.

If the contact section 70 is moved in a substantially horizontal direction though it is maintained contact with the affected part, the interlock is also established due to the rolling of the ball 71 of the contact section 70 in correspondence to the moving amount of the contact section 70.

The rolling of the ball 71 causes the rollers 73a and 73b to rotate. The rotation of the roller 73a (73b) is transmitted to the rotating disc 74a (74b). The rotation of the disc 74a (74b) is detected by the photosensor 76a (76b), which transmits a detection signal to the controller 15. The controller 15 detects that the contact section 70 (namely, the handpiece 20) is relatively moved with respect to the affected part based on the input detection signal in comparison with the signal from the photosensors 76a and 76b at the time of input of the trigger signal from the footswitch 9. The controller 15 stops the laser irradiation when the moving amount of the contact section 70 exceeds a predetermined amount. This moving amount can be obtained in the following manner. By the rotation of the rotating disc 74a (74b), the luminous flux projected by the light projecting element of the photosensor 76a (76b) is pulsed and received by the receiving element. The moving amount is thus calculated based on the number of pulses detected by the photosensor 76a (76b).

The above control can establish the interlock to stop the laser irradiation if the patient or the handpiece 20 unintentionally moves even during the laser irradiation, enabling the prevention of the laser irradiation to any parts other than the intended part.

As described above, in the above embodiments according to the present invention, the temperatures of the affected part and others are detected by the temp. sensors to prevent the laser irradiation to the affected part if it is not cooled enough for the laser irradiation, thereby reducing damage to the skin of the patient.

Detecting the contact/noncontact of the first window 42 with the affected part and the relative horizontal movement of the handpiece with respect to the affected part, the controller 15 operates to stop the laser irradiation when the affected part moves even during the laser irradiation. This makes it possible to prevent damage by the laser beam to unintended parts outside the affected part to be irradiated.

Moreover, the laser treatment apparatus provided with the cooling unit 35 constructed as above can appropriately cool the affected part in correspondence with the size of the laser irradiation area and also enhance the operability and the treatment efficiency of the apparatus.

The present invention may be embodied in other specific forms without departing from the spirit or essential characteristics thereof.

The foregoing description of the preferred embodiment of the invention has been presented for purposes of illustration and description. It is not intended to be exhaustive or to limit the invention to the precise form disclosed, and modifications and variations are possible in light of the above teachings or may be acquired from practice of the invention. The embodiment chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. A laser treatment apparatus which is used to treat an affected part of a patient's skin by irradiating a treatment laser beam to the affected part, the apparatus including:
    a laser irradiation unit provided with a laser irradiation optical system for delivering the laser beam to the affected part;
    a contact member including a contact face which is adapted to be brought into contact with the affected part;
    a cooler which cools the contact member via a conducting member;
    a contact sensor which detects whether the contact face is in a contact state or the contact face is in a non-contact state with respect to the affected part;
    a first temperature sensor which detects a first temperature of the affected part or the contact member;
    a second temperature sensor which detects a second temperature of the conducting member; and
    a temperature controller which controls cooling operations of the cooler based on a result of detection by the second temperature sensor when the contact sensor detects that the contact face is in the non-contact state, and based on a result of detection by the first temperature sensor when the contact sensor detects that the contact face is in the contact state.

2. The laser treatment apparatus according to claim 1 further including:
    an irradiation controller which enables laser irradiation after a lapse of a predetermined time when the contact sensor detects that the contact face is in the contact state.

3. The laser treatment apparatus according to claim 1, wherein the contact sensor detects whether the contact face is in the contact state or the contact face is in the non-contact state based on the result of detection by the first temperature sensor.

4. The laser treatment apparatus according to claim 1, wherein the contact member includes a laser transmission member made of material that is transmittable to the laser beam.

5. The laser treatment apparatus according to claim 1 further including:
an irradiation controller which controls laser irradiation based on a result of detection by the first temperature sensor.

6. The laser treatment apparatus according to claim 1 further including:
a movement sensor which detects a relative movement of the contact member in a substantially horizontal direction with respect to the affected part; and
an irradiation controller which controls laser irradiation based on a result of detection by the movement sensor.

7. A laser treatment apparatus which is used to treat an affected part of a patient's skin by irradiating a treatment laser beam to the affected part, the apparatus including:
a laser irradiation unit including a handpiece head provided with part of a laser irradiation optical system for delivering the laser beam to the affected part and an outlet through which the delivered laser beam is irradiated;
a window unit including a first window member having a contact face which is adapted to be brought into contact with the affected part, a second window member and a heat-insulating board arranged between the first and second window members so as to form a sealed space serving as a heat-insulating layer enclosed by the heat-insulating board between the first and second window members, the first and second window members each transmitting the laser beam irradiated through the outlet, the window unit adapted to support the handpiece head at a predetermined height on the affected part so that an operator can observe the affected part through the first and second window members; and
a cooler which cools the first window member.

8. The laser treatment apparatus according to claim 7, wherein the second window member has a lower thermal conductivity than the first window member.

9. The laser treatment apparatus according to claim 7, wherein the window unit includes a plurality of window units having different-sized first and second window members, each of the window units being detachable/attachable to the handpiece head.

10. A laser treatment apparatus which is used to treat an affected part of a patient's skin by irradiating a treatment laser beam to the affected part, the apparatus including:
a laser irradiation unit including a handpiece head provided with a part of a laser irradiation optical system for delivering the laser beam to the affected part and an outlet through which the delivered laser beam is irradiated;
a window unit including a first window member having a contact face which is adapted to be brought into contact with the affected part and a window frame which holds the first window member, the first window member and the window frame made of a material which is good in thermal conductivity, the first window member transmitting the laser beam irradiated through the outlet, the window unit adapted to support the handpiece head at a predetermined height on the affected part so that an operator can observe the affected part trough the first window member; and a cooler including a plate-shaped Peltier element as an electronic heat exchanger which has a heat-absorbing side surface and is disposed in the handpiece head so that the heat-absorbing side surface is perpendicular to the contact face of the first window member, the Peltier element cooling the window frame and the first window member by heat-absorbing of the window frame with the heat-absorbing side surface.

11. The laser treatment apparatus according to claim 10, wherein the handpiece head is provided with a window fixing member to which the window frame is detachable/attachable, the window fixing member is made of a material which is good in thermal conductivity, and the Peltier element cools the window frame and the first window member by heat-absorbing of the window frame via the window fixing member with the heat-absorbing side surface.

12. The laser treatment apparatus according to claim 10, wherein the window unit further includes a second window member and a heat-insulating member arranged between the first and second window members so as to form a sealed space serving as a heat-insulating layer enclosed by the heat-insulating member between the first and second window members, the second window member has a lower thermal conductivity than the first window member, and the first and second window members each transmits the laser beam irradiated through the outlet.

13. A laser treatment apparatus which is used to treat an affected part of a patient's skin by irradiating a treatment laser beam to the affected part, the apparatus including:
a laser irradiation unit including a handpiece head provided with a part of a laser irradiation optical system for delivering the laser beam to the affected part, a scanner which scans the laser beam and an outlet through which the delivered laser beam is irradiated;
a mode selecting unit with which a scan mode in which the scanner is allowed to be operated or a single mode in which the scanner is prohibited to be operated is selected;
a window unit including a first window member having a contact face which is adapted to be brought into contact with the affected part, the first window member transmitting the laser beam irradiated through the outlet, the window unit adapted to support the handpiece head at a predetermined height on the affected part so that an operator can observe the affected part through the first window member; and
a cooler which cools the first window member,
wherein the window unit includes a first window unit having a large-sized first window member to be used in the scan mode and a second window unit having a small-sized first window member to be used in the single mode, each of the first and second window units is detachable/attachable to the handpiece head.

14. The laser treatment apparatus according to claim 13, wherein the window unit further includes a second window member and a heat-insulating member arranged between the first and second window members so as to form a sealed space serving as a heat-insulating layer enclosed by the heat-insulating member between the first and second window members, and the first and second window members each transmits the laser beam irradiated through the outlet.

15. The laser treatment apparatus according to claim 13, wherein the cooler includes an electronic heat exchanger which is disposed in the handpiece head and cools the first window member.

* * * * *